US010217063B2

(12) United States Patent
Henderson et al.

(10) Patent No.: US 10,217,063 B2
(45) Date of Patent: Feb. 26, 2019

(54) SYSTEM AND METHOD FOR CLINICAL INTELLIGENT AGENTS IMPLEMENTING AN INTEGRATED INTELLIGENT MONITORING AND NOTIFICATION SYSTEM

(75) Inventors: Christine Henderson, Pittsburgh, PA (US); Lucy Thompson, Pittsburgh, PA (US); David T. Sharbaugh, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 283 days.

(21) Appl. No.: 12/648,343

(22) Filed: Dec. 29, 2009

(65) Prior Publication Data

US 2010/0169114 A1    Jul. 1, 2010

Related U.S. Application Data

(60) Provisional application No. 61/141,730, filed on Dec. 31, 2008.

(51) Int. Cl.
| | |
|---|---|
| *G06Q 10/00* | (2012.01) |
| *G06Q 50/22* | (2018.01) |
| *G16H 10/60* | (2018.01) |
| *G16H 50/20* | (2018.01) |

(52) U.S. Cl.
CPC ............ *G06Q 10/00* (2013.01); *G06Q 50/22* (2013.01); *G16H 10/60* (2018.01); *G16H 50/20* (2018.01)

(58) Field of Classification Search
CPC ........ G06Q 50/22; G06Q 50/24; G06Q 10/00; G16H 10/60; G16H 50/20

USPC .......................................................... 705/2, 3
See application file for complete search history.

(56) References Cited

U.S. PATENT DOCUMENTS

| | | | | |
|---|---|---|---|---|
| 6,999,565 B1* | 2/2006 | Delaney | ............... | G06Q 10/107 379/67.1 |
| 2003/0052787 A1* | 3/2003 | Zerhusen | ............. | A47B 23/046 340/573.1 |
| 2004/0262377 A1* | 12/2004 | Matz | .................... | A61B 5/0002 235/375 |
| 2006/0049936 A1* | 3/2006 | Collins, Jr. | ........... | A61B 5/1115 340/539.11 |
| 2006/0106641 A1* | 5/2006 | Bartsch | ............ | G06Q 10/06316 705/2 |
| 2006/0161457 A1* | 7/2006 | Rapaport | ............... | G06Q 10/10 705/2 |
| 2007/0156031 A1* | 7/2007 | Sullivan | ................. | G16H 40/20 600/300 |
| 2007/0244724 A1* | 10/2007 | Pendergast | .......... | G06F 19/3418 705/3 |
| 2008/0287746 A1* | 11/2008 | Reisman | ................ | G16H 50/20 600/300 |
| 2008/0312975 A2* | 12/2008 | Rosow | ................... | G06Q 10/02 705/5 |

(Continued)

*Primary Examiner* — Joy Chng
(74) *Attorney, Agent, or Firm* — Ference & Associates LLC

(57) ABSTRACT

A method includes: receiving patient specific data; comparing the patient specific data with reference data; producing alerts when the comparison determines that an event requiring action has occurred; and sending the alerts to care providers. An apparatus that implements the method and a computer readable medium including instructions for performing the method are also provided.

13 Claims, 1 Drawing Sheet

(56) References Cited

U.S. PATENT DOCUMENTS

| | | | |
|---|---|---|---|
| 2009/0105550 A1* | 4/2009 | Rothman | G06Q 50/22 600/300 |
| 2009/0216558 A1* | 8/2009 | Reisman | G06F 19/328 705/3 |
| 2009/0274384 A1* | 11/2009 | Jakobovits | G06F 19/321 382/254 |

* cited by examiner

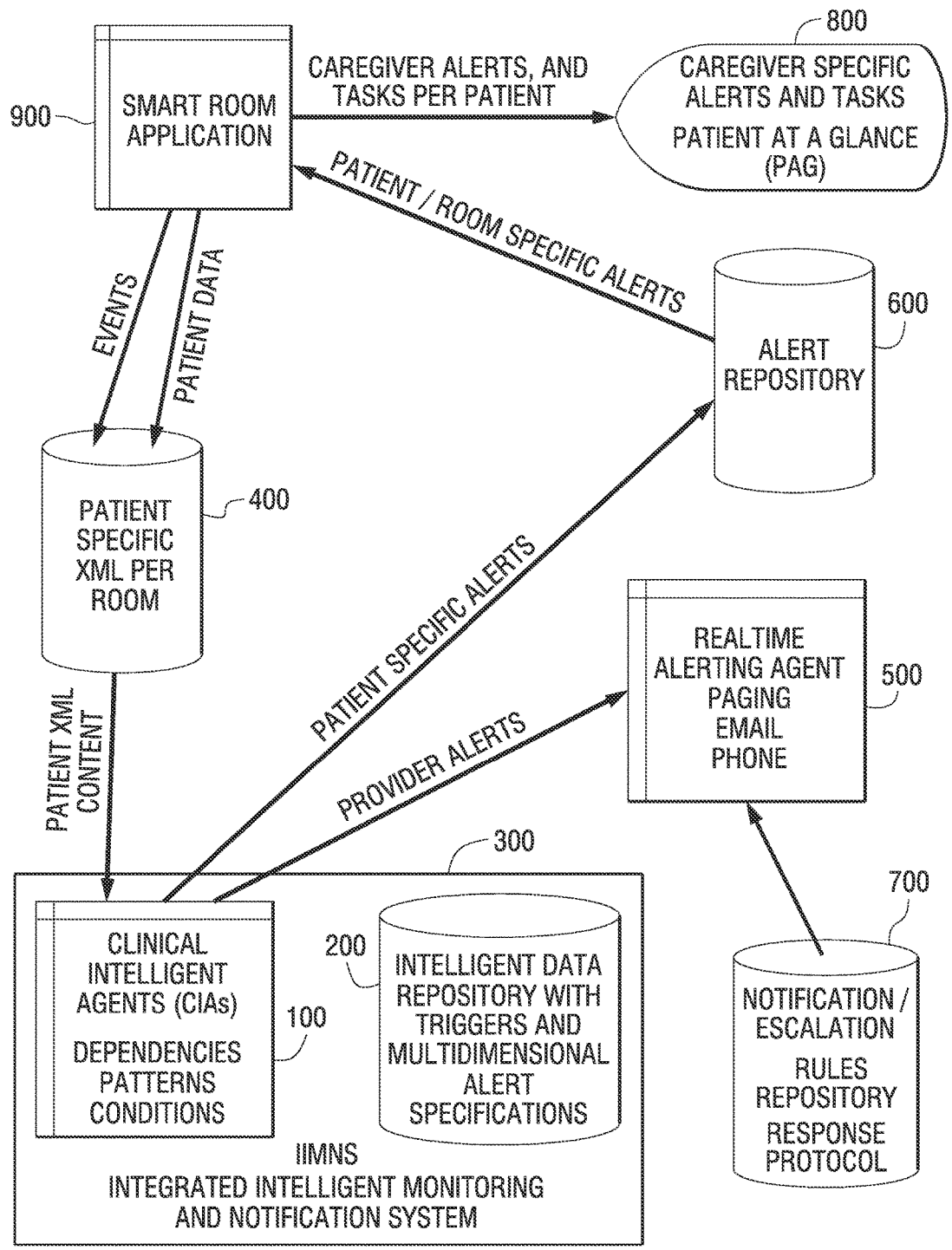

SYSTEM AND METHOD FOR CLINICAL INTELLIGENT AGENTS IMPLEMENTING AN INTEGRATED INTELLIGENT MONITORING AND NOTIFICATION SYSTEM

CROSS-REFERENCE TO RELATED APPLICATION

This application claims the benefit of U.S. Provisional Patent Application No. 61/141,730, filed Dec. 31, 2008, and titled "System And Method For Clinical Intelligent Agents Implementing An Integrated Intelligent Monitoring And Notification System", which is hereby incorporated by reference.

BACKGROUND OF THE INVENTION

Field of the Invention

The present invention relates to systems and methods for monitoring patient conditions and history and issuing notifications based on such monitoring.

Description of the Related Art

Events that trigger a need for patient care management require access to prompt communication of information for sound and prompt decision making and intervention.

Appropriate dissemination of timely information and the communication of critical events and specific details, such as background (historical information) with changing conditions and results, to the appropriate staff is vital to proactive intervention in patient care.

Effective communication and escalation based on severity and acceptable intervention response, and the automated management of this intervention is essential to effective response to a critical situation or the development of adverse conditions. The present state of this art is a manual monitoring of complex related information from disparate sources and manual monitoring of the progress.

The present state of the communication is informal and tenuous. As caregivers are notified, their response and changes in the circumstances are monitored.

Currently, there does not exist an efficient method to monitor critical events in patient care, disseminate the information, and then monitor the intervention and results, and produce historical reports for analysis.

SUMMARY OF THE INVENTION

In a first aspect, the invention provides a method that includes: receiving patient specific data; comparing the patient specific data with reference data; producing alerts when the comparison determines that an event requiring action has occurred; and sending the alerts to care providers.

In another aspect, the invention provides an apparatus including an input for receiving patient specific data; a data repository having reference data and trigger criteria; a processor for comparing the patient specific data with the reference data and issuing alerts when the trigger criteria are met; and an output for sending the alerts to care providers.

In another aspect, the invention provides a computer readable medium including instructions for configuring a computer system to receive patient specific data; compare the patient specific data with reference data and trigger criteria; provide alerts when the trigger criteria are met; and send the alerts to care providers.

BRIEF DESCRIPTION OF THE DRAWINGS

The drawing is a conceptual block diagram of a system in accordance with an embodiment of the present invention.

DETAILED DESCRIPTION OF THE INVENTION

In various aspects, the present invention relates to a system and method for clinical intelligent agents that monitor complex conditions and patient history to trigger alerts to an advanced notification system. The system and method can monitor complex situations that affect patient care and safety, and automatically generate alerts using multiple communication routes based on the severity of the situation with escalation capability. As used in this description, a clinical intelligent agent is a complex database model and application component that can be dynamically configured to detect clinical patterns, conditions, events that have occurred or should occur, and/or combinations of medical criteria to actively seek out impending conditions/situations in order to proactively react with appropriate remediation, tasks and notification processes.

As shown in the drawing, a typical implementation includes a clinical intelligent agent engine 100, and an intelligent data repository 200 with triggers and multidimensional alert specification capabilities, patient specific XML (Extensible Markup Language) per room 400, a real-time alerting agent with paging 500, an alerting repository 600, a notification/escalation rules repository with response protocol 700, caregiver specific alerts and tasks (which are broad in scope and context) routed to a patient at a glance display 800, and a smart room application with receivers 900. The clinical intelligent agent engine 100, and the intelligent data repository 200 are collectively referred to as an integrated intelligent monitoring and notification system 300. The integrated intelligent monitoring and notification system can be configured in any suitable manner as would be appreciated by one skilled in the art. Utilizing XML format enables seamless integration of data repositories for both inbound and outbound communication processes as well as dynamic analysis of the data based on the clinical intelligent agent monitoring criteria.

The clinical intelligent agent 100 includes an input for receiving patient specific information. It monitors conditions that exist with multiple dependencies and analyzes the conditions to detect a pattern that can be used to alert staff of potential concern. The patient specific data can be produced and delivered to the input in accordance with known techniques, including manual data entry and automatic transfer of information captured by various sensing devices.

The intelligent data repository 200 includes a complex database of reference data representative of health conditions and safety checks with related dependencies. The data includes trigger criteria that is used to determine if an event has occurred that requires action. Once such an event is detected, an alert is produced and sent via an output to an alerting agent. This repository can handle complex multidimensional monitors. These monitors can be implemented in software, and are designed to understand relationships between data and events without limit to the criteria involved. The monitors can relate to each other as well—the results of one monitor affecting the analysis of another. The monitors can analyze current data and events as well as historical events and patterns. The monitors can also analyze facility, tracking and clinical criteria, such as patient precaution or contamination, who (and when) was in contact with the patient, where the patient was and when, and relationship with overall facility (overall or specific to unit and/or room and/or bed) locations and personal as well as patient stay information—such as length of stay and associated alerts or processes. Additionally, the monitors can analyze the specific results of tasks and staff utilization and dynamically make assignment modifications to meet the demands and improve processes. For instance, these monitors can detect patterns of decompensation (clinical deterioration pattern) of a patient to proactively react, provide intervention and alert medical staff of the situation with escalation and notification procedures to automatically trigger at each stage appropriate for the specific pattern of decompensation and patient condition.

The alerting agent 500 includes software that analyzes medical records data and searches for conditions that meet the alert repository criteria. This system allows the collection, synthesis, updating and exchange of information needed to respond to the alert and communication state. The alert repository contains both current alerts and historical alerts. These alerts can be associated with any number of trigger criteria for extensive analysis of the data for decision support, to trigger real-time alerts and detail the current and past environment. The clinical intelligent agent configuration parameters contain the escalation criteria and apply these criteria to the alert or task or event to determine a current score. These alerts, tasks and events are monitored to escalate the score and/or notification as appropriate, based on the escalation criteria.

As alerts are produced, an alert is sent to the appropriate notification source and repository 600. The response to the alert is monitored and the alert can be escalated as appropriate using rules stored in a repository 700. Additional situational parameters can escalate or reduce the alert status based on changes in the situation. The escalation process uses a monitoring system to evaluate each alert or task or event and applies an associated algorithm to a plurality of parameters including a weighted value, incremental escalation value, multiplier, initial time to trigger, and elapsed time before triggering escalation levels (unlimited), and associated notification and events/tasks to trigger based on the level (unlimited)—this comprises the current score. These scores are also used to prioritize tasks and to dynamically change workload/assignments as well as for historical analysis processing. Notification processes trigger when scores reach defined levels.

As the caregiver enters the room, a patient at a glance screen (PAG) 800 can be used to display clinical intelligent agent alerting events 600, current caregiver tasks due within the hour with timestamps for due time, precautions, allergies and general patient information.

Examples of alerts based on status include: heart patient, medications change, labs become abnormal; dialysis patient/heart patient, fluid balance change, labs abnormal; patient flagged 'at risk' due to current regulatory requirements; and patient flagged 'at risk' due to current individual hospital initiatives.

In one embodiment, the clinical intelligent agent includes a plurality of components that can be implemented as software modules that run on one or more computers. The components include an alert event component, a conditions configuration component, and an agent alert pattern component.

The alert event component can provide a plurality of functions including: location tracking and trending by facility, unit, room and bed; patient tracking and trending; event time tracking; alert type, mode, categories and time tracking; pattern recognition; historical recording and reporting of events; remediation tracking for process improvement tied to associated conditions and events; dynamic customization; historical trending with dynamic abnormal pattern and condition alerts; dynamic modification of normal and abnormal values; and alert routing and escalation role notification roles to alert associations.

The conditions configuration component can include data elements with minimum, normal and critical value ranges, and can provide a course of action repository.

The agent alert event component can provide a plurality of functions including: pattern conditions; pattern relationships; a notification mode including notification parties, roles and levels; an escalation mode based on time and events, escalation incremental values, escalation time periods and stages; and precaution alerts.

The agent alert event component enables location tracking and trending by specific location, including for example, facility, unit, and room and/or bed breakdown. Additionally the component enables patient tracking and trending of the alerting events. These events can be time stamped to enable the historical detailed event state.

Alert types, mode and categories can be used to create pattern associations for triggers to create events.

Historic recording and monitoring of these events and patterns can be used to trigger additional alerts and notifications.

Remediation events are also tracked and can trigger process improvement events.

Components are tied to associated conditions and events which can be dynamically configured.

Events, patterns (normal and abnormal), and associations can be dynamically customized without modification of the application.

Alert routing, escalation, and role notifications are associated with each alert.

The conditions configuration component facilitates the use of minimum, normal and critical value ranges. These associations can be used to trigger a course of action event as defined in the repository.

The clinical intelligent agent alert pattern component embodies a pattern of conditions, relationships, a notification mode, notification roles, levels and parties, and an escalation mode based on time and events, escalation incremental weighted values to specify significance of time to event, escalation time period and stages, and precautionary alerts.

The clinical intelligent agents (CIAs) respond to a complex repository and monitoring system that analyzes a dynamic repository. It acts as an integrated intelligent monitoring and notification system (IIMNS). It is a large-scale automated communication system integrated into an intelligent database with triggers to provide for accurate patient situational awareness to the appropriate parties and/or caregiver.

This real-time tracking and notification system is event and data driven, with triggers for appropriate notification based on severity, incorporating automated escalation capability as well as tracking the intervention status and state of the response. This will result in a more efficient use of resources as well as a more timely response. Since all data will be captured, it will be available for historical event analysis using statistical algorithms to improve/enhance response measures and protocols based on past experience.

The above description describes a system and method for improved tracking and notification of patient condition and safety concerns. The functions illustrated in the FIGURE can be implemented in a computer or computer system, that is programmed to perform the functions and includes the hardware needed to input, store and process the data, and to produce alerts in the described method. In one embodiment, the invention can be implemented using a computer readable medium including instructions for configuring a computer system to receive patient specific data; process the patient specific data; provide alerts when the processing determines that action is needed; and notify care providers when the processing determines that action is needed.

While the invention has been described in terms of several embodiments, it will be apparent to those skilled in the art, that various changes can be made to the described embodiments without departing from the scope of the invention as set forth in the following claims.

What is claimed is:

1. A method comprising:
receiving, at a clinical intelligent agent, patient specific data comprising room location of a patient within a healthcare facility, at least one care provider having contact with the patient in the room location, and information regarding the condition of the patient in the room;
storing, at an intelligent data repository of the clinical intelligent agent, the patient specific data in a repository, the repository storing reference data including historical patient information derived from an electronic medical record;
using a processor to compare, using a monitor of the clinical intelligent agent, patient specific data with the reference data to detect clinical patterns and to identify an alert situation, wherein to identify an alert situation comprises detecting a pattern of decompensation with respect to the patient;
producing, using an alerting agent of the clinical intelligent agent, one or more alerts when the processor identifies a clinical pattern using the patient specific information and the reference data indicating an alert situation, wherein each alert situation is associated with a pattern of decompensation;
sending, using agent, the one or more alerts to an alert repository of the clinical intelligent agent;
storing the one or more alerts in the alert repository as one or more historical alerts for inclusion with the reference information;
sending, using the alerting agent, the one or more alerts to a patient screen located in the room occupied by the patient and accessible to the at least one care provider;
providing, using the clinical intelligent agent, a score to at least one alert situation identified, wherein the providing a score comprises applying escalation criteria to the detected pattern of decompensation;
prioritizing, using the clinical intelligent agent, care provider tasks displayed in the patient screen to dynamically change one or more of a workload and an assignment based on the score; and
as the at least one care provider enters the room, displaying on the patient screen located in the room current tasks for the at least one care provider and patient specific information for the patient in the room.

2. The method of claim 1, wherein the processor determines if the patient specific data exceeds trigger criteria in the reference data.

3. The method of claim 1 wherein the step of sending the one or more alerts comprises:
using predetermined notification rules to set a notification protocol for sending at least one of a page, e-mail or telephone call to care providers.

4. The method of claim 1, further comprising:
tracking and trending events identified by the processor based on a comparison of the patient specific data with the reference data.

5. The method of claim 4, wherein the events are time stamped to enable a historical detailed event state.

6. The method of claim 5, further comprising:
creating pattern associations for triggers used to identify the events.

7. The method of claim 4, further comprising:
recording and monitoring the events and patterns to trigger additional alerts.

8. The method of claim 1, further comprising:
tracking remediation actions to identify process improvements.

9. The method of claim 1, further comprising sending additional alerts using one or more of a plurality of communications routes based on a severity of the situation in accordance with escalation rules indicating a changed patient condition.

10. The method of claim 1, wherein the alert situation is based on one or more of a current regulatory requirement and a current individual hospital initiative.

11. The method of claim 1, wherein the alert situation is based on a current individual hospital initiative.

12. The method of claim 1, wherein at least one of the care provider tasks is organized in the patient screen as due within a predetermined time period and includes a time stamp for due time.

13. A system, comprising:
a patient at a glance screen located in a patient room having a patient therein; and
a monitoring system comprising a clinical intelligent agent operatively connected to the patient at a glance screen;
the monitoring system automatically acting to:
as a caregiver enters the room, display on the patient at a glance screen:
one or more alert events generated by an alerting agent of the monitoring system and specific to the patient currently in the room, wherein the one or more alert events are generated based upon comparing a current condition of the patient with historical patient information to identify a clinical pattern of decompensation with respect to the patient;
current caregiver tasks specific to the patient currently in the room and due within a predetermined time with timestamps for due time, wherein the current caregiver tasks are organized based on the one or more alert events, wherein the current caregiver tasks are based upon a score determined by applying escalation criteria to the identified clinical pattern of decompensation; and
at least one item of patient information specific to the patient currently in the room and selected from the group consisting of precaution information and allergy information.

* * * * *